United States Patent
Ito et al.

(10) Patent No.: US 10,696,785 B2
(45) Date of Patent: Jun. 30, 2020

(54) DIOL COMPOSITION AND POLYESTER

(75) Inventors: Masateru Ito, Kamakura (JP); Izumi Morita, Tokai (JP); Kenji Kawamura, Kamakura (JP); Tetsuya Yamada, Kamakura (JP); Sadanori Kumazawa, Nagoya (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 269 days.

(21) Appl. No.: 14/000,897

(22) PCT Filed: Feb. 21, 2012

(86) PCT No.: PCT/JP2012/054069
§ 371 (c)(1),
(2), (4) Date: Oct. 8, 2013

(87) PCT Pub. No.: WO2012/115084
PCT Pub. Date: Aug. 30, 2012

(65) Prior Publication Data
US 2014/0296471 A1    Oct. 2, 2014

(30) Foreign Application Priority Data
Feb. 22, 2011 (JP) .................... 2011-035839

(51) Int. Cl.
*C08G 63/16* (2006.01)
*C07C 31/20* (2006.01)

(52) U.S. Cl.
CPC ............. *C08G 63/16* (2013.01); *C07C 31/20* (2013.01)

(58) Field of Classification Search
None
See application file for complete search history.

(56) References Cited

U.S. PATENT DOCUMENTS

| 5,576,397 A | 11/1996 | Oberressl et al. | |
| 5,877,262 A | 3/1999 | Saito | |
| 2007/0241306 A1 | 10/2007 | Wehner et al. | |
| 2008/0275277 A1* | 11/2008 | Kalagias | B01D 3/14 568/854 |
| 2009/0171037 A1* | 7/2009 | Aoshima | C08G 63/16 525/418 |

FOREIGN PATENT DOCUMENTS

| EP | 1 882 712 A1 | 1/2008 | |
| JP | 05-038291 A | 2/1993 | |
| JP | 07-002994 A | 1/1995 | |
| JP | 09-003181 A | 1/1997 | |
| JP | 11-196888 A | 7/1999 | |
| JP | 2002-020596 | 1/2002 | |
| JP | 2005-298547 A | 10/2005 | |
| JP | 2006-219514 A | 8/2006 | |
| JP | 2007-502325 A | 2/2007 | |
| JP | 2008-094888 A | 4/2008 | |
| JP | 2008094884 | * | 4/2008 |
| JP | 4380654 B2 | 12/2009 | |
| JP | 2010-150248 A | 7/2010 | |
| WO | 2004/101479 A2 | 11/2004 | |
| WO | 2005/073364 A2 | 8/2005 | |
| WO | 2007/097260 A1 | 8/2007 | |
| WO | 2009/076377 | 6/2009 | |

OTHER PUBLICATIONS

Minh et al., Top Catal (2010) 53:1270-1273.*
"Technical Bulletin, Susterra™ Propanediol, A Renewable Resource for Unsaturated Polyester Resins" DuPont Tate & Lyle BioProducts, Jul. 9, 2008 at http://www2.dupont.com/Bio-based_Propanediol/zh_CN/assets/downloads/DT&L%20Technical%20Bulletin%20-%20Susterra(r)%20in%20UPR's%2007-28-08.pdf (last visited Nov. 8, 2016).*
Susterra® Propanediol, Product Data Sheet, DuPont Tate & Lyle BioProducts at http://www2.dupont.com/Bio-based_Propanediol/zh_CN/assets/downloads/Susterra(r)%20PU%20Technical%20Data%20April%202010.pdf (last visited Nov. 8, 2016).*
Database CAPLUS Chemical Abstracts Service, Columbus, Ohio, US; Database Accession No. 2008:496486, Abstract of JP 2008094884, Mitsubishi Chemical Corp., Japan, Ueda et al., Apr. 24, 2008.*
Machine Translation of JP 2008094884 (2008) retrieved from URL: https://patents.google.com/patent/JP2008094884A/en on Jan. 4, 2018.*
Karen M. Drafts et al., "Environmentally Compatible Synthesis of Adipic Acid from $_D$-Glucose", Sep. 17, 1993, *J. Am. Chem. Soc.* 1994, vol. 116, pp. 399-400.
English translation of a Notice of Final Rejection dated Aug. 29, 2018, of counterpart Korean Application No. 10-2013-7020908.
Examination Report dated Sep. 18, 2018, of counterpart Indian Application No. 6308/CHENP/2013, with English translation.
Z.L. Xiu et al., "Present state and perspective of downstream processing of biologically produced 1, 3-propanediol and 2,3-butanediol", *Applied Microbiology and Biotechnology*, (2008), 78(6), pp. 917-926.
Patent Examination Report No. 1 dated Mar. 23, 2015 of corresponding Australian Application No. 2012221259.
New Zealandern First Examination Report dated May 16, 2014 from corresponding New Zealandern Patent Application No. 614029.

* cited by examiner

*Primary Examiner* — Karl J Puttlitz
(74) *Attorney, Agent, or Firm* — DLA Piper LLP (US)

(57) ABSTRACT

A diol composition includes a diol as a major component and has an electrical conductivity of 0.6 to 30 mS/m.

11 Claims, No Drawings

DIOL COMPOSITION AND POLYESTER

TECHNICAL FIELD

This disclosure relates to a diol composition comprising a diol as a major component, which composition is used as a polyester material, and to a polyester made from the diol composition.

BACKGROUND

Polyester has been used in a wide variety of applications including fibers, films, and bottles because of its excellent properties. For example, polyethylene terephthalate, which is obtained by polycondensation of ethylene glycol and terephthalic acid, has been used in many applications because of its excellent mechanical strength, chemical properties, and the like, and mass-produced around the world as a synthetic fiber most suitable for clothes. For example, for polytrimethylene terephthalate which is made from 1,3-propanediol and terephthalic acid, its market is expanding because inexpensive 1,3-propanediol synthesis methods have been developed in recent years, and polytrimethylene terephthalate is expected to be used for clothes of soft texture making use of polymer properties such as excellent elastic recovery after elongation and a low Young's modulus.

In more recent years, biomass resource-derived polyesters have received attention out of concern about steep price increase and depletion of petroleum resources. In addition to polylactic acid obtained by polymerizing lactic acid obtained by a fermentation method, polybutylene succinate obtained by synthesizing a monomer through chemical conversion of succinic acid obtained by a fermentation method and polymerizing the monomer has been developed as a biomass resource-derived polyester (Japanese Patent No. 4380654). Biomass resource-derived polyester materials have a problem in that biomass resource-derived impurities may be contained, and as a means for solving the problem, methods of removing biomass resource-derived impurities using a nanofiltration membrane have been developed (JP 2007-502325 W and JP 2010-150248 A).

Polyester is formed into various molded articles by molding, and it is known that polyester degradation occurs during its melt molding, which degradation is generally expressed as a thermal weight loss rate. A high thermal weight loss rate can cause deterioration in mechanical properties of resin or reduce molding stability.

Polyethylene terephthalate, polytrimethylene terephthalate, and polybutylene terephthalate having an aromatic backbone have been developed as a polyester having a low thermal weight loss rate, and further reducing the thermal weight loss rate of these polyesters further enhances their physical properties and, in addition, enables high-speed molding at high temperature.

Thus, it could be helpful to provide a method of producing a polyester having a lower thermal weight loss rate and more excellent mechanical properties and molding stability than those of conventional polyesters.

SUMMARY

We discovered that controlling the electrical conductivity of a diol composition used as a polyester material reduces the thermal weight loss rate of a polyester and provides a polyester with excellent mechanical properties and molding processability.

We thus provide (1) to (7):
(1) A diol composition comprising a diol as a major component and having an electrical conductivity of 0.6 to 30 mS/m.
(2) The diol composition according to (1), having a pH in the range of 5 to 7.5.
(3) The diol composition according to (1) or (2), comprising a biomass resource-derived diol.
(4) The diol composition according to any one of (1) to (3), comprising a linear aliphatic diol as a major component.
(5) The diol composition according to any one of (1) to (4), wherein the linear aliphatic diol is ethylene glycol, 1,3-propanediol, 1,2-propanediol, 1,3-butanediol, 1,4-butanediol, or 2,3-butanediol.
(6) A polyester made from the diol composition according to any one of (1) to (5) and a dicarboxylic acid.
(7) A molded article produced by molding the polyester according to (6).

We provide a polyester having a reduced thermal weight loss rate and, in addition, excellent color tone while maintaining the performance of conventional polyesters. Furthermore, the polyester obtained has excellent mechanical properties and molding stability and, in addition, enables high-speed molding using melt molding at high temperature, and, consequently, physical properties of a molded article and productivity will be improved compared to conventional polyesters.

DETAILED DESCRIPTION

The diol composition is characterized by comprising a diol as a major component and, in addition, a substance that contributes to electrical conductivity as a minor component (hereinafter referred to as "minor component substance"). Diol is a general term for compounds having two hydroxyl groups and known to be used with dicarboxylic acid as a material of polyester. It is known that diol itself does not have electrical conductivity. Specific examples of diols include linear aliphatic diols such as ethylene glycol, 1,3-propanediol, 1,2-propanediol, 1,3-butanediol, 1,4-butanediol, 2,3-butanediol, 1,5-pentanediol, 1,2-pentanediol, 1,3-pentanediol, 1,4-pentanediol, neopentyl glycol, 1,6-hexanediol, 1,7-heptanediol, 1,8-octanediol, 1,9-nonanediol, 1,10-decanediol, diethylene glycol, polyethylene glycol, polypropylene glycol, and polytetramethylene glycol; branched aliphatic diols such as 2-methyl 1,3-propanediol, 3-methyl-1,5-pentanediol, 2-methyl-1,8-octanediol, and 2,2-diethyl-1,3-propanediol; cyclic aliphatic diols such as 1,2-cyclohexanediol, 1,4-cyclohexanediol, 1,2-cyclohexanedimethanol, 1,4-cyclohexanedimethanol, 1,3-cyclobutanediol, 2,2,4,4,-tetramethyl-1,3-cyclobutanediol, hydrogenated bisphenol A, isosorbide, isomannide, and isoidide; and, further, aromatic diols such as hydroquinone, resorcin, dihydroxybiphenyl, naphthalene diol, dihydroxybenzene, and dihydroxytoluene. In the diol composition, at least one of these diols may be contained, and two or more diols may be contained. The diol content in the diol composition is preferably 95% by weight or more, and more preferably 99% by weight or more.

Examples of minor component substances contained in the diol composition include organic acids, amino acids, amines, and ammonia, carbon dioxide, and the like. Specific examples of organic acids include oxalic acid, acetic acid, lactic acid, formic acid, pyruvic acid, propionic acid, malonic acid, succinic acid, citric acid, glycolic acid, malic acid, n-butyric acid, isobutyric acid, hydroxy butyric acid, α-ketoglutaric acid, maleic acid, tartaric acid, glyoxylic acid, citraconic acid, pyroglutaric acid, and ascorbic acid, which may be used alone or in combination. These minor component substances have hitherto been presumed to be a substance causing coloration of polyester, and containing these minor component substances in the diol composition for polyester material has hitherto been avoided. However, our composition positively contains these minor component substances to control the electrical conductivity of a diol composition and using the diol composition as a polyester material to thereby reduce the thermal weight loss rate of a polyester.

Specifically, the diol composition is characterized by having an electrical conductivity of 0.6 to 30 mS/m because of containing minor component substances. The electrical conductivity of the diol composition is a value indicating the rate of electrical conductivity measured when a platinum black electrode is immersed in an aqueous diol composition solution at 23° C. with a diol composition concentration of 16.67% by weight, and the electrical conductivity can be measured using an electrical conductivity cell in an apparatus for water quality determination. The electrical conductivity of the diol composition is correlated with the content of the minor component substances in the diol composition, and, therefore, the electrical conductivity of the diol composition can be controlled by controlling the content of the minor component substances. When the electrical conductivity of the diol composition is within this range, the thermal weight loss rate of a polyester made from the diol composition decreases. However, an electrical conductivity of less than 0.6 mS/m or less is not preferred because it increases the thermal weight loss rate of a polyester, and an electrical conductivity of more than 30 mS/m is not preferred because it inhibits polyester polymerization and reduces the molecular weight, melting point, and yield of a polyester. From the standpoint of preventing the coloration of polyester due to the minor component substances, the upper limit of the electrical conductivity of the diol composition is preferably not more than 10 mS/m, and more preferably not more than 3 mS/m.

The diol composition preferably has a pH in the range of 5 to 7.5. The pH of the diol composition is a pH of an aqueous diol composition solution at 23° C. with a diol composition concentration of 16.67% by weight. When the pH is less than 5, by-product generation and yield decrease can be caused in polyester polymerization. When the pH is higher than 7.5, the same will happen as in the case of a pH less than 5, and when, in addition, an amine compound is present in an excess amount, coloration of polyester and foul smell can be caused. The pH is more preferably in the range of 6 to 7. The pH of the diol composition can be controlled by appropriately adding acid or alkali within the electrical conductivity range of 0.6 to 30 mS.

When the diol contained in the diol composition is a purified diol obtained through a combination of known organic chemical catalytic reactions from acetylene, maleic anhydride, or propylene oxide made from petroleum (hereinafter referred to as petroleum-derived diol), the minor component substances mentioned above are not contained as impurities, or infinitesimal if contained, and thus the electrical conductivity of the diol composition can be controlled to be in a desired range by appropriately adding the minor component substances to the purified diol.

When the diol contained in the diol composition is a diol made from biomass resources (hereinafter referred to as biomass resource-derived diol), biomass-derived minor component substances can be contained as impurities during the process for producing a diol, and thus the amount of the minor component substances contained in the diol composition can be controlled by controlling the diol purification process, by which, in turn, the electrical conductivity of the diol composition can be controlled.

Specific examples of biomass resources include monosaccharides such as hexoses such as glucose, mannose, galactose, fructose, sorbose, and tagatose and pentoses such as arabinose, xylose, ribose, xylulose, and ribulose; disaccharides/polysaccharides such as pentosan, sucrose, starch, and cellulose; fatty acids such as butyric acid, caproic acid, caprylic acid, capric acid, lauric acid, myristic acid, palmitin acid, palmitoleic acid, stearic acid, oleic acid, linoleic acid, linolenic acid, monocutinic acid, arachidic acid, eicosenoic acid, arachidonic acid, behenic acid, erucic acid, docosapentaenoic acid, docosahexaenoic acid, lignoceric acid, and ceracoreic acid; and polyalcohols such as glycerin, mannitol, xylitol, and ribitol.

The biomass resource-derived diol may be obtained from biomass resources through a combination of known organic chemical catalytic reactions, may be obtained by converting an intermediate product such as dicarboxylic acid, dicarboxylic anhydride, or cyclic ether obtained by culturing microorganisms capable of assimilating biomass resources into a diol by chemical reaction, or may be obtained directly by culturing microorganisms that are capable of assimilating biomass resources.

For a method of obtaining a diol from biomass resources through a combination of known organic chemical catalytic reactions, for example, when using pentose as a biomass resource, a diol such as butanediol can be readily obtained through a combination of a known dehydration reaction and catalytic reaction.

One of the known methods of converting a biomass resource-derived intermediate product into a diol by chemical reaction is to hydrogenate dicarboxylic acid obtained by known microbial culture with a reduction catalyst to obtain a diol. In the case of 1,4-butanediol, examples of the method include conversion of, for example, succinic acid, succinic anhydride, succinic acid ester, maleic acid, maleic anhydride, maleic acid ester, tetrahydrofuran, or γ-butyrolactone obtained by known microbial culture into 1,4-butanediol by chemical synthesis, and obtaining 1,4-butanediol by hydrogenating succinic acid with a reduction catalyst is efficient and preferred.

Examples of known methods of obtaining a diol directly by fermentation of microorganisms that are capable of assimilating biomass resources include the method of producing 1,3-propanediol or 1,4-butanediol described in WO2007/097260, the method of producing 1,2-propanediol described in WO2005/073364, and the method of producing ethylene glycol described in Japanese Patent No. 4380654. Furthermore, it is fully anticipated that with the recent development of microbial metabolic engineering and genetic engineering, processes for obtaining various diols directly by culturing microorganisms will be developed in the future.

Preferred biomass resource-derived diols are, in view of the known technological level of diol production, linear aliphatic diols such as ethylene glycol, 1,3-propanediol, 1,2-propanediol, 1,3-butanediol, 1,4-butanediol, 2,3-butanediol, 1,5-pentanediol, 1,2-pentanediol, 1,3-pentanediol, 1,4-pentanediol, neopentyl glycol, diethylene glycol, 1,6-hexanediol, 1,7-heptanediol, 1,8-octanediol, 1,9-nonanediol, 1,10-decanediol, diethylene glycol, polyethylene glycol, polypropylene glycol, and polytetramethylene glycol, and ethylene glycol, 1,3-propanediol, 1,2-propanediol, 1,3-butanediol, 1,4-butanediol, and 2,3-butanediol are more preferred.

To prepare the diol composition from a petroleum-derived diol, minor component substances may be appropriately added to the petroleum-derived diol because minor component substances are not contained in the petroleum-derived diol as mentioned above.

In the method of preparing the diol composition from a biomass resource-derived diol, in cases where the diol is obtained by chemical reaction of a biomass resource-derived intermediate product, biomass resource-derived minor component substances are sometimes removed during the stage of purification of the intermediate product, in which case minor component substances may be added as appropriate. In cases where the diol is obtained directly by culturing microorganisms capable of assimilating biomass resources, purification of a diol-containing culture solution enables controlling the content of biomass resource-derived minor component substances and controlling the electrical conductivity of the diol composition. As mentioned above, minor component substances that can be contained in a biomass resource-derived diol have been presumed to be a substance causing degradation of color tone of polyester, and an object of the prior art has been to remove biomass resource-derived minor component substances as much as possible by highly purifying a biomass resource-derived diol-containing solution. Therefore, a technological idea has never been known that purification is intentionally carried out such that biomass resource-derived minor component substances remain to thereby control the electrical conductivity of a diol composition. For example, JP 2007-502325 W discloses a method of highly purifying diol using nanofiltration membrane purification, but the electrical conductivity of a diol composition obtained by this method is estimated to be lower than 0.6 mS/m (see JP 2007-502325 W, paragraph [0130]). Furthermore, JP 2010-150248 A discloses a method of purifying a diol-containing solution, but the electrical conductivity of a diol composition obtained by this method has been proven to be higher than 30 mS/m from our experimental results (see the Examples). Thus, we discovered that a desired electrical conductivity can be achieved by improving the purification method described in JP 2010-150248 A and incorporating an electrodialysis step (Step B) between a nanofiltration membrane purification step (Step A) and a distillation step (Step C) (see the Examples).

A method in which Steps A to C are combined, which method is an improved method of the diol purification method described in JP 2010-150248 A mentioned above, will now be described in detail as an example of methods of producing our diol composition.

The nanofiltration membrane purification step (Step A) can be performed in accordance with the method described in JP 2010-150248 A. The nanofiltration membrane used is preferably a nanofiltration membrane containing polyamide as a functional layer, and more preferably a nanofiltration membrane containing bridged piperazine polyamide as a major component and polyamide containing a component represented by Formula (I) below as a functional layer:

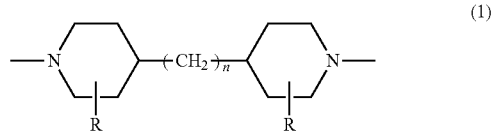

(1)

wherein R represents —H or —CH$_3$, and n represents an integer from 0 to 3.

The diol-containing solution obtained in Step A is preferably concentrated because if the diol concentration is low, great energy is required in the subsequent Step C to remove water having a boiling point lower than that of diol. A common method of concentrating a nanofiltration membrane-permeated solution is a method using a concentrator such as an evaporator, which method is applicable herein, but the energy and time required for concentration are huge because the heat capacity of water is much higher than those of organic solvents. Concentration using a reverse osmosis membrane is superior to concentration using an evaporator in terms of energy/cost reduction and preferably used. The step of concentrating a diol-containing solution using a reverse osmosis membrane can be performed in accordance with the method described in JP 2010-150248 A.

From the diol-containing solution obtained in Step A, minor component substances remaining after the nanofiltration membrane purification step can be further removed by the electrodialysis step (Step B). Electrodialysis is a method of removing ionic substances from a diol-containing solution through cation exchange membranes and anion-exchange membranes. There are ion-exchange membranes with a molecular weight cut-off of, for example, 100, 300, or 500, which can be appropriately selected.

The distillation step (Step C) can be performed in accordance with the method described in JP 2010-150248 A.

Furthermore, to control the electrical conductivity by purifying a diol-containing culture solution, absorbents may be used. Activated carbon, zeolite, synthetic resins, and the like are known as an absorbent. When removing hydrophobic components, activated carbon is preferred, and when removing hydrophilic components, hydrophilized zeolite or synthetic resin is preferably employed.

Furthermore, the diol-containing solution may be crystallized. Crystallization is a process in which a highly-concentrated diol composition is cooled to its melting point or lower and crystallized products are separated from impurities by filtration. Crystallization is preferred because of high selectivity of similar compounds and a high purifying effect. However, since huge energy is required for cooling and it can be difficult to separate viscous compounds by filtration, crystallization is preferably employed for diol compositions of high value.

Dicarboxylic acid, which is used as a material of polyester together with our diol compositions, may be synthesized by a petrochemical method (organic synthesis method), may be produced from microorganisms by a fermentation method, or may be produced by a combination of a petrochemical method and a fermentation method.

Specific examples of dicarboxylic acids include aromatic dicarboxylic acids, aliphatic dicarboxylic acids, and alicyclic dicarboxylic acids. Examples of aromatic dicarboxylic acids include terephthalic acid, isophthalic acid, naphthalene dicarboxylic acid, phthalic acid, diphenyldicarboxylic acid, diphenyl ether dicarboxylic acid, diphenoxyethane dicarboxylic acid, and 5-sodium sulfoisophthalic acid; examples of aliphatic dicarboxylic acids include oxalic acid, succinic acid, adipic acid, sebacic acid, dimer acid, maleic acid, and fumaric acid; and examples of alicyclic dicarboxylic acids include 1,4-cyclohexanedicarboxylic acid and decalindicarboxylic acid. Furthermore, the dicarboxylic acid may be a dicarboxylic acid obtained from biomass by a fermentation method. Examples thereof include succinic acid obtained by growing recombinant bacteria of *Brevibacterium flavum*, an aerobic coryneform bacterium, and then allowing the bacteria to act on an organic raw material anaerobically in a carbon dioxide-containing solution (JP 11-196888 A). Furthermore, the dicarboxylic acid may be a dicarboxylic acid obtained by a combination of chemical reaction and enzyme reaction using biomass or products of microorganism fermentation as a precursor. Examples thereof include oxalic acid obtained by enzyme reaction of oxamide (JP 05-38291 A), adipic acid obtained by hydrogenation reaction of muconic acid using recombinant *E. coli* (Journal of American Chemical Society No. 116 (1994) 399-400), and sebacic acid obtained from castor oil. Any of these dicarboxylic acids can be preferably used; aromatic dicarboxylic acids are preferred, and terephthalic acid is more preferred.

For a method of producing a polyester made from our diol composition and a dicarboxylic acid, a known method can be used. For example, the polyester can be produced by performing an esterification reaction or a transesterification reaction of a diol composition with a dicarboxylic acid or with a dicarboxylic acid component comprising an ester-forming derivative thereof, and a subsequent polycondensation reaction. Any reactions such as solution reaction using a solvent and melting reaction in which heat melting is performed may be used, but the melting reaction is preferred because a polyester of good quality can be obtained efficiently. The catalyst and solvent used in the reaction may be controlled according to the diol composition and the dicarboxylic acid component. Specifically, transesterification methods and direct polymerization methods are known as a method of producing a polyester. For example, a transesterification method using a dialkyl ester of an aromatic dicarboxylic acid and our diol composition, a method in which polycondensation reaction is carried out after synthesizing an ester of an aromatic dicarboxylic acid and our diol composition, or a direct polymerization reaction of an aliphatic dicarboxylic acid with the diol composition may be used. In the esterification reaction or transesterification reaction and the subsequent polycondensation reaction, a batch method or a continuous method can be employed. In each reaction, any reaction vessel can be used, such as stirring vessel-type reaction vessels, mixer-type reaction vessels, tower-type reaction vessels, extruder-type reaction vessels, and the like. These reaction vessels can be used in combination of two or more thereof.

In the esterification reaction or transesterification reaction and the subsequent polycondensation reaction, catalysts may be used to promote the reaction. As a compound that acts as a catalyst, specifically, titanium compounds, tin compounds, aluminum compounds, calcium compounds, lithium compounds, magnesium compounds, cobalt compounds, manganese compounds, antimony compounds, germanium compounds, zinc compounds, and the like are preferred because they are highly reactive and can increase the reaction rate and yield of the resulting polyester. Examples of transesterification catalysts include alkali metal acetates, and examples of polymerization catalysts include germanium oxide, antimony oxide with little contamination, for example, by bismuth, in addition, transition metal compounds such as cobalt, and alkoxy titanate. Among them, titanium compounds, tin compounds, aluminum compounds, antimony compounds, and germanium compounds are preferred because the reaction time can be reduced to achieve efficient production; titanium compounds and/or tin compounds are more preferred because crystallization properties are easily controlled and a polyester having excellent qualities such as thermal stability, hydrolysis resistance, and thermal conductivity can be obtained; and titanium compounds are still more preferred because they are environmentally friendly. Examples of titanium compounds include titanic acid esters such as tetra-n-propyl ester, tetra-n-butyl ester, tetraisopropyl ester, tetraisobutyl ester, tetra-tert-butyl ester, cyclohexyl ester, phenyl ester, benzyl ester, tolyl ester, and mixed-esters thereof. Above all, tetrapropyl titanate, tetrabutyl titanate, and tetraisopropyl titanate are preferred because polyester resin can be produced efficiently, and, in particular, tetra-n-butyl titanate and the like are preferably used. Examples of tin compounds include monobutyltin oxide, dibutyltin oxide, methylphenyltin oxide, tetraethyltin oxide, hexaethylditin oxide, cyclohexahexylditin oxide, didodecyltin oxide, triethyltin hydroxide, triphenyltin hydroxide, triisobutyltin acetate, dibutyltin diacetate, diphenyltin dilaurate, monobutyltin trichloride, dibutyltin dichloride, tributyltin chloride, dibutyltin sulfide, butylhydroxytin oxide, methyl stannoic acid, ethyl stannoic acid, and butyl stannoic acid, among which, in particular, monoalkyltin compounds are preferably used because polyesters can be efficiently produced. Such compounds that act as a catalyst may be used alone or in combination in the esterification reaction or transesterification reaction and the subsequent polycondensation reaction. For the timing of addition, any method such as adding immediately after the addition of raw materials, adding together with raw materials, or adding during the reaction can be used. The amount of the compounds that act as a catalyst is, in the case of titanium compounds, preferably 0.01 to 0.3 parts by weight based on 100 parts by weight of the polyester produced. In terms of thermal stability, hue, and reactivity of the polymer, it is more preferably 0.02 to 0.2 parts by weight, and still more preferably 0.03 to 0.15 parts by weight.

In producing the polyester, usual additives, for example, one or more of UV absorbers, heat stabilizers, lubricants, releasing agents, coloring agents including dyes and pigments, and the like can be added to improve heat resistance, hue, weatherability, durability, or the like as long as the desired effect is not impaired.

The polyester is a polyester obtained using the diol composition and the dicarboxylic acid described above as raw materials, specific example of which include the following polyesters.

Examples of polyesters made from a diol composition comprising ethylene glycol as a major component include polyester of the diol composition and succinic acid (polyethylene succinate), polyester of the diol composition and adipic acid (polyethylene adipate), polyester of the diol composition and succinic acid and adipic acid, polyester of the diol composition and oxalic acid, polyester of the diol composition and sebacic acid, polyester of the diol composition and terephthalic acid (polyethylene terephthalate), and polyester of the diol composition and naphthalene dicarboxylic acid (polyethylene naphthalate).

Examples of polyesters made from a diol composition comprising 1,3-propanediol as a major component include polyester of the diol composition and succinic acid, polyester of the diol composition and adipic acid (polytrimethylene adipate), polyester of the diol composition and succinic acid and adipic acid, polyester of the diol composition and oxalic acid, polyester of the diol composition and sebacic acid (polytrimethylene sebacate), and polyester of the diol composition and terephthalic acid (polytrimethylene terephthalate).

Examples of polyesters made from a diol composition comprising 1,2-propanediol as a major component include polyester of the diol composition and succinic acid, polyester of the diol composition and adipic acid, polyester of the diol composition and succinic acid and adipic acid, polyester of the diol composition and oxalic acid, polyester of the diol composition and sebacic acid, and polyester of the diol composition and terephthalic acid.

Examples of polyesters made from a diol composition comprising 1,3-butanediol as a major component include polyester of the diol composition and succinic acid, polyester of the diol composition and adipic acid, polyester of the diol composition and succinic acid and adipic acid, polyester of the diol composition and oxalic acid, polyester of the diol composition and sebacic acid, and polyester of the diol composition and terephthalic acid.

Examples of polyesters made from a diol composition comprising 1,4-butanediol as a major component include polyester of the diol composition and succinic acid (polybutylene succinate), polyester of the diol composition and adipic acid, polyester of the diol composition and succinic acid and adipic acid (polybutylene succinate adipate), polyester of the diol composition and oxalic acid, polyester of the diol composition and sebacic acid, polyester of the diol composition and terephthalic acid (polybutylene terephthalate), polyester of the diol composition and succinic acid and terephthalic acid (polybutylene succinate terephthalate), and polyester of the diol composition and naphthalene dicarboxylic acid (polybutylene naphthalate).

Examples of polyesters made from a diol composition comprising 2,3-butanediol as a major component include polyester of the diol composition and succinic acid, polyester of the diol composition and adipic acid, polyester of the diol composition and succinic acid and adipic acid, polyester of the diol composition and oxalic acid, polyester of the diol composition and sebacic acid, and polyester of the diol composition and terephthalic acid.

Furthermore, copolyesters obtained by adding a copolymer component as a third component to the diol composition and the dicarboxylic acid described above is also included in the polyester. Specific examples of copolymer components include at least one polyfunctional compound selected from the group consisting of bifunctional hydroxycarboxylic acids, tri- or more functional (to form a cross-linked structure) polyhydric alcohols, tri- or more functional polycarboxylic acids and/or anhydrides thereof, and tri- or more functional hydroxycarboxylic acids. Among these copolymer components, in particular, bifunctional and/or tri- or more functional hydroxycarboxylic acids are suitably used because there is a tendency that highly-polymerized copolyester can be readily produced. Above all, using a tri- or more functional hydroxycarboxylic acid is the most preferred method because, even if used in very small amounts, highly-polymerized polyester can be readily produced without using a chain extender mentioned below. Specific examples of copolyesters include polyesters comprising lactic acid as a third component (e.g., polybutylene succinate lactate) and polyesters comprising bisphenol A as a third component (e.g., polybutylene succinate carbonate).

One of the characteristics of the physical property values of the polyester is that by using a diol composition having an electrical conductivity of 0.6 to 30 mS/m as a raw material, the thermal weight loss rate is reduced compared to polyesters made from known diols. The thermal weight loss rate is a value of the weight loss rate calculated when a polyester sample has been retained for a given time at or near the melting point of the polyester. For example, it is a value calculated from a weight after 10 minutes after heating to the measurement temperature (W1), so that there is no influence of water/solvent contained in the polyester, and a weight after 30 minutes after heating (W2) using Equation (1) below:

Thermal weight loss rate (%)={(W1−W2)/W1}×100     (1).

The preferred thermal weight loss rate of the polyester calculated by Equation (1) can vary depending on the type of polyester, but, in general, it is preferably 0.3% or lower, more preferably 0.2% or lower, and still more preferably 0.1% or lower. Even if a polyester has a thermal weight loss rate slightly higher than 0.3%, the polyester is at a usable level as commodity plastics. However, since the polyester is formed under melting conditions, when the thermal weight loss rate of the polyester is 0.3% or lower, a high-quality polyester molded article having excellent mechanical properties and molding stability can be obtained, and, in addition, high-speed molding can be performed because the polyester withstands melt molding at high temperature. Within the range of 0.3% or lower, the lower the thermal weight loss rate of the polyester is, the higher the quality of the resulting polyester molded article is.

Furthermore, when the electrical conductivity of a diol composition, a polyester material, is 0.6 to 30 mS/m, a polyester excellent also in color tone is provided. The color tone is determined with yellowness (YI value), and the upper limit of the yellowness (YI value) of the polyester is preferably not higher than 30, more preferably not higher than 20, and still more preferably not higher than 10. Even if a polyester has a YI value higher than 30, the polyester is usable enough as commodity plastics because the influence on mechanical properties of the polyester is slight. However, a YI not higher than 30 provides a higher-quality polyester molded article with excellent color tone. Herein, the YI value is a value calculated by the method according to JIS K7105.

The polyester may be blended with commodity thermoplastic resins as appropriate to use the resulting resin composition for various applications. Examples of commodity thermoplastic resins include polyolefin resins such as polyethylene, polypropylene, ethylene-vinyl acetate copolymer, and ethylene-α-olefin copolymer; halogen-containing resins such as polyvinyl chloride, polyvinylidene chloride, chlorinated polyolefins, and polyvinylidene fluoride; styrene resins such as polystyrene and acrylonitrile-butadiene-styrene copolymer; polyester resins such as polyethylene terephthalate and polybutylene terephthalate; elastomers such as polyisoprene, polybutadiene, acrylonitrile-butadiene copolymer rubber, styrene-butadiene copolymer rubber, and styrene-isoprene copolymer rubber; polyamide resins such as nylon 6,6 and nylon 6; furthermore, polyvinyl acetate; methacrylate resins; polycarbonate resins; polyacetal; polyphenylene oxide; and polyurethane. Various compatibilizers may be used in combination to control various properties.

Furthermore, the polyester may be blended with various conventionally known additives to use the resulting composition for various applications. Examples of additives include additives for resin such as crystal nucleating agents, antioxidants, antiblocking agents, UV absorbers, light stabilizers, plasticizers, heat stabilizers, coloring agents, flame retardants, mold releasing agents, antistatic agents, antifogging agents, surface wettability-improvers, burning agents, pigments, lubricants, dispersing agents, and various surfactants.

Furthermore, the polyester may be blended with various conventionally known fillers to use the resulting composition for various applications.

Examples of inorganic fillers include anhydrous silica, mica, talc, titanium oxide, calcium carbonate, diatomaceous earth, allophane, bentonite, potassium titanate, zeolite, sepiolite, smectite, kaolin, kaolinite, glass fibers, limestone, carbon, wollastonite, calcined pearlite, and salts such as silicates (e.g., calcium silicate and sodium silicate), aluminum oxide, magnesium carbonate, hydroxides (e.g., calcium hydroxide), ferric carbonate, zinc oxide, iron oxide, aluminum phosphate, and barium sulfate.

Examples of organic fillers include raw starch, modified starch, pulp, chitinlchitosan, coconut shell powder, wood powder, bamboo powder, bark powder, and powder of kenaf, straw, and the like.

To the preparation of the composition described above, every conventionally known mixing/kneading technique can be applied. Examples of mixers that can be used include horizontal cylindrical mixers, V-shaped mixers, double cone mixers, blenders such as ribbon blenders and super mixers, and various continuous mixers. Examples of kneaders that can be used include batch-type kneaders such as rolls and internal mixers, one-stage and two-stage continuous kneaders, twin-screw extruders, and single-screw extruders. Examples of kneading methods include a method in which various additives, fillers, and thermoplastic resins are added to a heated melt and mixed. Furthermore, blending oil or the like can also be used to disperse the various additives described above uniformly.

The polyester can be subjected to a known molding method applicable to commodity plastics to obtain a molded article. Examples of molding methods include compression molding (compression molding, lamination molding, stampable molding), injection molding, extrusion molding and coextrusion molding (film extrusion by inflation method or T-die method, lamination, sheet extrusion, pipe extrusion, wire/cable extrusion, profile extrusion), hollow molding (various blow moldings), calendaring, foam molding (melt foam molding, solid-phase foam molding), solid forming (uniaxial stretching, biaxial stretching, rolling, formation of oriented nonwoven fabric, thermoforming [vacuum forming, air-pressure forming], plastic forming), powder molding (rotation molding), and various nonwoven fabric forming (dry method, adhesion method, entanglement method, spunbond method, and the like).

By the molding methods described above, various molded articles can be obtained, such as monolayer film, multilayer film, stretched film, shrink film, laminate film, monolayer sheet, multilayer sheet, stretched sheet, pipe, wire/cable, monofilament, multifilament, various nonwoven fabrics, flat yarn, staple, crimped fibers, stretched tape or band, striated tape, split yarn, composite fibers, blow bottle, and foam. The molded articles obtained are expected to be used for shopping bags, garbage bags, various films such as agricultural films, various containers such as cosmetic containers, detergent containers, food containers, and containers for bleaching agent, clothes, fishing lines, fishing nets, ropes, binding materials, surgical thread, sanitary cover stock materials, cooling boxes, buffer materials, medical materials, electric appliance materials, housings for household appliances, automobile materials, civil engineering and construction materials, stationery, and the like.

EXAMPLES

Our compositions and methods will now be described in detail, but this disclosure is not limited to the following examples. The property values in the examples were determined by the following measurement methods.
A. Electrical Conductivity of Diol Composition To a multi water quality meter (MM-60R, manufactured by DKK-TOA CORPORATION), an electrical conductivity cell for low electrical conductivity (CT-57101C, manufactured by DKK-TOA CORPORATION) was mounted, and immersed in an aqueous diol composition solution at 23° C. with a diol composition concentration of 16.67% by weight to measure the electrical conductivity. The measured value obtained was multiplied by 6 to calculate the electrical conductivity of the diol composition.
B. pH of Diol Composition To a multi water quality meter (MM-60R, manufactured by DKK-TOA CORPORATION), a pH combination electrode for organic solvent (ELP-031, manufactured by DKK-TOA CORPORATION) was mounted, and immersed in an aqueous diol composition solution at 23° C. with a diol composition concentration of 16.67% by weight for 30 minutes to measure the pH.
C. Thermal Weight Loss Rate of Polyester A polyester sample in an amount of 10 mg was placed in a thermogravimetric analyzer (TG/DTA7200, manufactured by SII NanoTechnology Inc.) and held at 250° C. The weight after holding at 250° C. for 10 minutes (W1) and the weight after 30 minutes (W2) were measured, and the weight loss rate was calculated using Equation 1 described above.
D. YI Value of Polyester To evaluate the hue of a polyester, measurements were made using a color tone measuring apparatus (SZ-Σ80 Model colorimeter, manufactured by NIPPON DENSHOKU INDUSTORIES CO., LTD.) in accordance with JIS K7105.

Comparative Example 1: Polyester Made from Petroleum-Derived 1,3-Propanediol

To a 304 g of 1,3-propanediol having an electrical conductivity of 0.1 mS/m and a pH of 7.5 (available from Wako Pure Chemical Industries, Ltd.), 388 g of dimethyl terephthalate (available from Wako Pure Chemical Industries, Ltd.) and tetrabutyl titanate as a catalyst were added, and esterification reaction was carried out at 140° C. to 230° C. with stirring. Furthermore, polycondensation reaction was carried out for 3 hours under fixed conditions of 250° C. temperature to obtain a polytrimethylene terephthalate prepolymer. The prepolymer obtained was predried at 120° C. for 1 hour, and then solid-phase polymerized at 200° C. for 4 hours under a reduced pressure of 1.2 to 0.7 hPa to obtain polytrimethylene terephthalate (PTT). The thermal weight loss rate of the PTT obtained was measured to be 0.33%. The YI value of the PTT was 6.

Examples 1 to 3: Polyester Made from Petroleum-Derived 1,3-Propanediol Composition (with Propionic Acid Added)

To 304 g of the petroleum-derived 1,3-propanediol (available from Wako Pure Chemical Industries, Ltd.) of Comparative Example 1, propionic acid (available from Wako Pure Chemical Industries, Ltd.) was added in an amount of 0.4 g (Example 1), 1.0 g (Example 2), and 3.9 g (Example 3) to prepare diol compositions. The electrical conductivities of the diol compositions were 0.7 mS/m, 1.3 mS/m, and 4.8 mS/m, and the pHs were pH 6.2, pH 5.7, and pH 5.1. To the 1,3-propanediol composition obtained, 388 g of dimethyl terephthalate and tetrabutyl titanate as a catalyst were added, and the same procedure as in Comparative Example 1 was carried out for polymerization of PTT. The thermal weight loss rates of the PTTs obtained were measured to be 0.27% (Example 1), 0.28% (Example 2), and 0.28% (Example 3). The YI values of the PTTs were 6 (Example 1), 7 (Example 2), and 6 (Example 3).

Example 4: Polyester Made from Biomass Resource-Derived 1,3-Propanediol Composition Preparation of Biomass Resource-Derived Diol Composition A biomass resource-derived 1,3-propanediol-containing culture solution obtained according to the method described in Example 19 of WO2007/097260 was filtered through a nanofiltration membrane (SU-610: available from TORAY INDUSTRIES, INC.) to filter out impurities to the non-permeate side of the membrane, and a permeate purified solution containing 1,3-propanediol was recovered from the permeated side. The permeate purified solution was subjected to electrodialysis to remove cationic impurities and anionic impurities. Micro Acilyzer EX3B (manufactured by ASTOM Corporation.) was used as an electrodialyser, and dedicated cartridges (effective membrane area: 550 cm$^2$) were used as a cation- and anion-exchange membrane. Using 1 N sodium hydroxide as an electrolyte solution, electrodialysis was carried out at 30 V, and passing a current was stopped when the current value reached 0.2 A or less. The 1,3-propanediol-containing solution was then recovered and concentrated in an evaporator. Furthermore, the 1,3-propanediol concentrated solution was distilled under reduced pressure (5 mmHg, still temperature: 130° C.) to distill off low-boiling components including water, and then a diol composition comprising 1,3-propanediol as a major component was obtained. The 1,3-propanediol composition obtained had an electrical conductivity of 28 mS/m and a pH of 5.1.

Thermal Weight Loss Rate and YI Value of Polyester

The 1,3-propanediol composition described above in an amount of 304 g was polycondensated in the same manner as in Comparative Example 1 to obtain PTT. The thermal weight loss rate of the PTT was measured to be 0.30%. The YI value of the PTT was 15, which was somewhat higher than the values of the petroleum-derived 1,3-propanediol compositions, but the PTT had excellent quality sufficient to be used as polyester.

Comparative Example 2: Polyester Made from Biomass Resource-Derived 1,3-Propanediol Composition Preparation of Biomass Resource-Derived Diol Composition A 1,3-propanediol culture solution produced in the same manner as in Example 4 was concentrated without carrying out desalting, and then the resulting inorganic salt precipitate was removed. The resultant was subjected to distillation under reduced pressure (5 mmHg, still temperature: 130° C.) to obtain a 1,3-propanediol composition. The 1,3-propanediol composition obtained had an electrical conductivity of 65 mS/m and a pH of 3.2.

Thermal Weight Loss Rate and YI Value of Polyester

For PTT obtained by polycondensating the 1,3-propanediol composition described above in the same manner as in Comparative Example 1, the thermal weight loss rate was measured to be as high as 0.45%. Moreover, the PTT was brown, and the YI value was 58, showing that the quality decreased also in color tone.

Comparative Example 3: Polyester Made from Biomass Resource-Derived 1,3-Propanediol Composition Preparation of Biomass Resource-Derived Diol Composition A 1,3-propanediol culture solution prepared in the same manner as in Example 4 was purified according to the production method described in JP 2010-150248 A. Specifically, the 1,3-propanediol culture solution was first filtered through a nanofiltration membrane (SU-610: available from TORAY INDUSTRIES, INC.) to filter out impurities to the non-permeate side of the membrane, and a permeate purified solution containing 1,3-propanediol was recovered from the permeated side. Consequently, the brown culture solution became a clear 1,3-propanediol-containing solution. The 1,3-propanediol solution was filtered through a reverse osmosis membrane (SU-810, available from TORAY INDUSTRIES, INC.) to filter out water to the permeated side of the membrane for concentration, and then further concentrated using an evaporator. This crude 1,3-propanediol solution was distilled under reduced pressure in the same manner as in Example 4 to obtain a 1,3-propanediol composition having an electrical conductivity of 32 mS/m and a pH of 4.8.

Thermal Weight Loss Rate and YI Value of Polyester

For PTT obtained by polycondensating the 1,3-propanediol composition described above in the same manner as in Comparative Example 1, the thermal weight loss rate was measured to be as high as 0.40%. The YI value of the PTT was 35.

TABLE 1

|  |  | Comparative Example 1 | Example 1 | Example 2 | Example 3 | Example 4 | Comparative Example 2 | Comparative Example 3 |
|---|---|---|---|---|---|---|---|---|
| 1,3-PDO Composition | Electrical Conductivity [mS/m] | 0.1 | 0.7 | 1.3 | 4.8 | 28 | 65 | 32 |
|  | pH | 7.5 | 6.2 | 5.7 | 5.1 | 5.1 | 3.2 | 4.8 |
| PTT Properties | Hue (Y.I) | 6 | 6 | 7 | 6 | 15 | 58 | 30 |
|  | Thermal Weight Loss Rate [%] | 0.33 | 0.27 | 0.28 | 0.30 | 0.28 | 0.45 | 0.40 |

Comparative Example 4: Polyester Made from Petroleum-Derived 1,4-Butanediol

Thermal Weight Loss Rate and YI Value of Polyester

The electrical conductivity and pH of petroleum-derived 1,4-butanediol (available from Wako Pure Chemical Industries, Ltd.) was measured; the electrical conductivity was 0.3 mS/m, and the pH was 7.5. First, to carry out esterification reaction, 54.2 g of the 1,4-butanediol was mixed with 113.2 g of terephthalic acid (available from Wako Pure Chemical Industries, Ltd.), and 0.08 g of tetra-n-butyl titanate as a catalyst and 0.07 g of monobutyl hydroxy tin oxide were added. The resulting mixture was allowed to react in a reactor equipped with a rectifying column under conditions 190° C. and 79.9 kPa, and 68.5 g of 1,4-butanediol (molar final concentration: 1,4-butanediol/terephthalic acid=2/1) was slowly added while gradually increasing the temperature to obtain a esterification reactant. To 125 g of the esterification reactant, 0.08 g of tetra-n-butyl titanate and 0.01 g of phosphoric acid as a polycondensation catalyst were added, and polycondensation reaction was carried out under conditions of 250° C. and 67 Pa. The polybutylene terephthalate (PBT) produced had a thermal weight loss rate of 0.37% and a YI value of 8.

Comparative Example 5: Polyester Resin Made from Biomass Resource-Derived 1,4-Butanediol Composition Preparation of Biomass Resource-Derived Succinic Acid To 100 mL of medium for seed culture heat-sterilized at 121° C. and 2 atmospheres for 20 minutes, the medium containing 20 g/L of glucose, 10 g/L of polypeptone, 5 g/L of yeast extract, 3 g/L of dipotassium hydrogen phosphate, 1 g/L of sodium chloride, 1 g/L of ammonium sulfate, 0.2 g/L of magnesium chloride hexahydrate, and 0.2 g/L of calcium chloride dihydrate, 1 mL of 30 mM sodium carbonate and 0.15 mL of 180 mM sulfuric acid were added in an anaerobic glove box, and 0.5 mL of a reducing solution containing 0.25 g/L of cysteine/HCl and 0.25 g/L of sodium sulfide was further added. Thereafter, *Anaerobiospirillum succiniciproducens* ATCC 53488 was inoculated, and static culture was performed at 39° C. overnight to prepare a preculture solution.

Next, into 3 L of fermentation medium heat-sterilized at 121° C. and 2 atmospheres for 20 minutes, the fermentation medium containing 50 g/L of glucose, 10 g/L of polypeptone, 5 g/L of yeast extract, 1 g/L of dipotassium hydrogen phosphate, 0.4 g/L of ammonium chloride, 0.2 g/L of calcium chloride dihydrate, 0.2 g/L of magnesium chloride hexahydrate, and 0.001 g/L of iron sulfate heptahydrate, $CO_2$ gas was bubbled from a sparger at 10 mL/min, and after adding 30 mL of 3 M sodium carbonate, pH was adjusted to 6.8 with a sulfuric acid solution. Thereafter, 1.5 mL of a reducing solution containing 0.25 g/L of cysteine/HCl and 0.25 g/L of sodium sulfide was added and 50 mL of the preculture solution described above was inoculated, and main culture was performed at a stirring rate of 200 rpm and 39° C. for 39 hours. During the culture, 5 M calcium hydroxide was used to adjust the pH of the culture solution to be 6.4.

HPLC analysis of the succinic acid culture solution under the following measurement conditions showed that the accumulated amount of succinic acid was 117 g.

HPLC Analysis Conditions

Column: Shim-Pack SPR-H (available from Shimadzu Corporation), 45° C.
Mobile phase: 5 mM p-toluenesulfonic acid 0.8 mL/min
Reaction solution: 5 mM p-toluenesulfonic acid, 20 mM Bistris, 0.1 M EDTA/2Na (0.8 mL/min)
Detector: Electrical conductivity The culture solution was sterilized by heating at 120° C. for 20 minutes and then centrifuged at 5000 g for 20 minutes. The supernatant was recovered to obtain a calcium succinate-containing culture solution. Sulfuric acid was added to the culture supernatant, and purified calcium sulfate was separated to obtain an aqueous succinic acid solution, which was further purified using a nanofiltration membrane similarly to Example 4, and water was removed in an evaporator while heating to 60° C. The supersaturated solution was gradually cooled and allowed to stand at 4° C. overnight to crystallize succinic acid, and the succinic acid was obtained by solid-liquid separation.

Preparation of 1,4-Butanediol Composition Made from Biomass Resource-Derived Succinic Acid Hydrogenate reaction of succinic acid was performed according to Examples in Japanese Patent No. 4380654 to obtain a 1,4-butanediol composition. Specifically, to 105 g of the succinic acid described above, 333 g of methanol and 2.1 g of concentrated sulfuric acid were added and reacted with stirring under reflux for 2 hours. After cooling the reaction solution, 3.8 g of sodium hydrogen carbonate was added and stirred at 60° C. for 30 minutes. The resulting mixture was distilled under normal pressure, and then the distillation residue was filtered and distilled under reduced pressure to obtain dimethyl succinate. To the dimethyl succinate, CuO—ZnO catalyst was added, and the resultant was stirred under hydrogen at 5 MPa in a pressure reaction vessel while increasing the temperature to 230° C. over 1 hour. Thereafter, the resulting mixture was reacted at 230° C. for 9 hours under hydrogen pressure of 15 MPa, and degassed after cooling. The catalyst was removed from the reaction solution by filtration, and the filtrate was distilled under reduced pressure to obtain a 1,4-butanediol composition. The 1,4-butanediol composition obtained had an electrical conductivity of 0.5 mS/m and showed a pH of 6.5.

Thermal Weight Loss Rate and YI Value of Polyester

Using 122.7 g of the 1,4-butanediol composition described above, PBT was obtained in the same manner as in Comparative Example 4. The PBT obtained had a thermal weight loss rate of 0.35% and a YI value of 10.

Example 5: Polyester Made from Biomass Resource-Derived 1,4-Butanediol Composition (with Isobutyric Acid Added)

Thermal Weight Loss Rate and YI Value of Polyester

To 112.7 g of the biomass resource-derived 1,4-butanediol obtained in Comparative Example 5, 0.1 g of isobutyric acid was added to prepare a 1,4-butanediol composition having an electrical conductivity of 0.9 mS/m and a pH of 6.3. Using the diol composition, esterification reaction and polycondensation reaction were carried out in the same manner as in Comparative Example 4 to obtain PBT. The PBT obtained had a thermal weight loss rate of 0.28% and a YI value of 10.

TABLE 2

| | | Comparative Example 4 | Comparative Example 5 | Example 5 |
|---|---|---|---|---|
| 1,4-BDO Composition | Electrical Conductivity [mS/m] | 0.3 | 0.5 | 0.9 |
| | pH | 7.5 | 6.5 | 6.3 |
| PBT Properties | Hue (Y.I) | 8 | 10 | 10 |
| | Thermal Weight Loss Rate [%] | 0.37 | 0.35 | 0.28 |

Example 6: Polyester Made from Biomass Resource-Derived 1,4-Butanediol Composition (with Malic Acid and Lactic Acid Added) and Biomass Resource-Derived Succinic Acid Preparation of Biomass Resource-Derived Diol Composition To 49.6 g of the biomass resource-derived 1,4-butanediol obtained in Comparative Example 5, 0.2 g of malic acid (available from Tokyo Chemical Industry Co., Ltd.) and 3.2 g of 90% by weight aqueous lactic acid solution (available from Wako Pure Chemical Industries, Ltd.) were added. The 1,4-butanediol composition obtained had an electrical conductivity of 1.2 mS/m and a pH of 5.2.

Thermal Weight Loss Rate and YI Value of Polyester

To 53.0 g of the 1,4-butanediol composition described above, 59.1 g of the biomass resource-derived succinic acid obtained in Comparative Example 5 was added, and 0.032 g of germanium dioxide (available from Wako Pure Chemical Industries, Ltd.) was added as a catalyst. The resulting mixture was allowed to react in a nitrogen atmosphere at 180° C. for 0.5 hours, and allowed to react for 0.5 hours after increasing the temperature to 220° C. Subsequently, the temperature was increased to 230° C. over 0.5 hours while reducing the pressure to 67 Pa over 1.5 hours, and polymerization reaction was carried out at this reduced pressure for 2.5 hours. The polybutylene succinate (PBS) obtained had a thermal weight loss rate of 0.07% and a YI value of 10.

Comparative Example 6: Polyester Made from Petroleum-Derived 1,4-Butanediol Composition (with Malic Acid and Lactic Acid Added) and Biomass Resource-Derived Succinic Acid Preparation of Petroleum-Derived Diol Composition To 49.6 g of the petroleum-derived 1,4-butanediol used in Comparative Example 4, 0.2 g of malic acid (available from Tokyo Chemical Industry Co., Ltd.) and 3.2 g of 90% by weight aqueous lactic acid solution (available from Wako Pure Chemical Industries, Ltd.) were added. The 1,4-butanediol composition obtained had an electrical conductivity of 0.5 mS/m and a pH of 5.2.

Thermal Weight Loss Rate and YI Value of Polyester

To 53.0 g of the 1,4-butanediol composition described above, 59.1 g of the biomass resource-derived succinic acid obtained in Comparative Example 5 was added, and 0.032 g of germanium dioxide (available from Wako Pure Chemical Industries, Ltd.) was added as a catalyst. PBS was obtained in the same manner as in Example 6. The PBS obtained had a thermal weight loss rate of 0.23% and a YI value of 10.

TABLE 3

| | | Example 6 | Comparative Example 6 |
|---|---|---|---|
| 1,4-BDO Composition | Electrical Conductivity [mS/m] | 1.2 | 0.5 |
| | pH | 5.2 | 5.2 |
| PBS Properties | Hue (Y.I) | 10 | 10 |
| | Thermal Weight Loss Rate [%] | 0.07 | 0.23 |

INDUSTRIAL APPLICABILITY

The diol composition can be used as a polyester material. The polyester has a reduced thermal weight loss rate and excellent color tone compared to conventional polyesters and thus can be used as industrial plastic.

The invention claimed is:

1. A diol composition comprising:
   1) 95% by weight or more of a diol selected from the group consisting of ethylene glycol, 1,3-propanediol, 1,2-propanediol, 1,3-butanediol, 1,4-butanediol, and 2,3-butanediol, and
   2) one or more components selected from the group consisting of oxalic acid, acetic acid, lactic acid, formic acid, pyruvic acid, propionic acid, malonic acid, succinic acid, citric acid, glycolic acid, malic acid, n-butyric acid, isobutyric acid, hydroxy butyric acid, α-ketoglutaric acid, maleic acid, tartaric acid, glyoxylic acid, citraconic acid, pyroglutaric acid, and ascorbic acid in an amount sufficient to cause the diol composition to have an electrical conductivity of 0.6 to 30 mS/m as determined by measuring electrical conductivity as an aqueous diol composition solution at 23° C. with a diol composition concentration of 16.67% and multiplying the measured conductivity by 6.

2. The diol composition according to claim 1, having a pH of 5 to 7.5.

3. The diol composition according to claim 1, comprising a biomass resource-derived diol.

4. The diol composition according to claim 2, comprising a biomass resource-derived diol.

5. A polyester made from the diol composition according to claim 2 and a dicarboxylic acid.

6. A polyester made from the diol composition according to claim 3 and a dicarboxylic acid.

7. A method of producing polyester comprising:
   producing polyester using the dial composition according to claim 1 and a dicarboxylic acid as materials.

8. A method of producing polyester comprising:
   producing polyester using the diol composition according to claim 1 and a dicarboxylic acid as materials; and
   producing a molded article by molding said polyester.

9. A diol composition comprising:
   1) 95% by weight or more of a dial selected from the group consisting of ethylene glycol, 1,2-propanediol, 1,3-butanediol, 1,4-butanediol, and 2,3-butanediol, and
   2) one or more components selected from the group consisting of oxalic acid, acetic acid, lactic acid, formic acid, pyruvic acid, propionic acid, malonic acid, succinic acid, citric acid, glycolic acid, malic acid, n-butyric acid, isobutyric acid, hydroxy butyric acid, α-ketoglutaric acid, maleic acid, tartaric acid, glyoxylic acid, citraconic acid, pyroglutaric acid, and ascorbic acid in an amount sufficient to cause the diol composition to have an electrical conductivity of 0.6 to 30 mS/m as determined by measuring electrical conductivity as an aqueous diol composition solution at 23° C. with a diol composition concentration of 16.67% and multiplying the measured conductivity by 6.

10. A polyester made from the diol composition according to claim 1 and a dicarboxylic acid.

11. A molded article produced by molding the polyester according to claim 10.

* * * * *

UNITED STATES PATENT AND TRADEMARK OFFICE
CERTIFICATE OF CORRECTION

| | | |
|---|---|---|
| PATENT NO. | : 10,696,785 B2 | Page 1 of 1 |
| APPLICATION NO. | : 14/000897 | |
| DATED | : June 30, 2020 | |
| INVENTOR(S) | : Ito et al. | |

It is certified that error appears in the above-identified patent and that said Letters Patent is hereby corrected as shown below:

In the Specification

<u>In Column 3</u>
At Line 31, please delete "or less".

Signed and Sealed this
Third Day of August, 2021

Drew Hirshfeld
*Performing the Functions and Duties of the
Under Secretary of Commerce for Intellectual Property and
Director of the United States Patent and Trademark Office*